United States Patent
Schrof et al.

(10) Patent No.: US 7,274,459 B2
(45) Date of Patent: Sep. 25, 2007

(54) METHOD AND DEVICE FOR ANALYSING BLUSHING IN DISPERSION FILMS

(75) Inventors: Wolfgang Schrof, Neuleiningen (DE);
Thorsten Müller, Ludwigshafen (DE);
Alexander Centner, Neustadt (DE);
Stephan Lehmann, Ludwigshafen (DE); Joachim Hadeler, Frankenthal (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 451 days.

(21) Appl. No.: 10/499,632

(22) PCT Filed: Jan. 13, 2003

(86) PCT No.: PCT/EP03/00233
§ 371 (c)(1),
(2), (4) Date: Jun. 21, 2004

(87) PCT Pub. No.: WO03/058216
PCT Pub. Date: Jul. 17, 2003

(65) Prior Publication Data
US 2005/0014282 A1    Jan. 20, 2005

(30) Foreign Application Priority Data
Jan. 14, 2002    (DE) ................. 102 01 075

(51) Int. Cl.
*G01N 21/47*    (2006.01)

(52) U.S. Cl. ....................................... 356/446
(58) Field of Classification Search ........ 356/445–448, 356/239.1
See application file for complete search history.

(56) References Cited

U.S. PATENT DOCUMENTS

| 4,072,426 | A | 2/1978 | Horn |
| 4,687,338 | A | 8/1987 | Task et al. |
| 5,155,558 | A | 10/1992 | Tannenbaum et al. |
| 6,268,218 | B1 | 7/2001 | Pantoliano et al. |
| 6,559,939 | B1 * | 5/2003 | Saunders ................. 356/239.1 |

FOREIGN PATENT DOCUMENTS

EP    1 030 173    8/2000

* cited by examiner

*Primary Examiner*—Layla G. Lauchman
(74) *Attorney, Agent, or Firm*—Novak Druce & Quigg LLP

(57) ABSTRACT

A process for parallel and automated evaluation of the blushing of multiple samples of dispersion films, comprising: providing an illuminated array of spatially separated samples of dispersion films, imaging the array of samples by means of CCD camera at different times and digitizing the images, automatically determining multiple brightness for each sample at different times from the different digitized images for at least a portion of the samples, determining values of a parameter characteristic of the kinetics of the blushing from the different brightnesses, and comparing the values of the characteristic parameter for individual samples.

4 Claims, 2 Drawing Sheets

METHOD AND DEVICE FOR ANALYSING BLUSHING IN DISPERSION FILMS

The invention relates to a process and to a device for evaluating the blushing of dispersion films.

Blushing is when initially clear dispersion films become cloudy. It may take place immediately after production of the film or when the film later comes into contact with water. Blushing is caused by separation phenomena in the dispersion film or an ingress of water droplets, which lead to light scattering and opalescence.

The degree of blushing of dispersion films is usually determined using spectrocolorimeters or opacimeters as well as the naked eye.

Visual inspection is subjective and varies with the individual observer. Nor is the determination of the kinetics of blushing with high precision possible by visual inspection. Spectrolorimeters and opacimeters are relatively complicated and expensive instruments. A high sample throughput of several hundred or several thousand samples in a short time is not achievable by the methods mentioned.

U.S. Pat. No. 4,072,426 discloses a process and a device for determining the reflective characteristics of coated surfaces. A converging lens is used therein to create a beam of parallel light rays from the light emitted by a light source and directing it onto the reflecting surface to be investigated. The light which is regularly reflected by the surface is focused by means of a second converging lens onto a first receiver, for example a light-sensitive resistor. The majority of the scattered light is masked out by a circular diaphragm surrounding the receiver and the light passing through the ring opening is focused by means of a concave mirror located behind the diaphragm onto a second receiver disposed on the reverse of the first receiver.

EP-A 1 030 173 discloses a process for automatic inspection of a moving surface, for example a metal film. This involves illuminating the moving surface with two or more pulsed light sources from different directions, each at different times, the pulse frequency being >1 kHz. The illuminated surface region is imaged as lines by means of a line scan camera in sync with the light pulses. The process serves to recognize surface anomalies.

It is an object of the invention to find a process for evaluating blushing of dispersion films which is simple to implement and facilitates a high sample throughput.

We have found that this object is achieved by a process for parallel and automated evaluation of the blushing of n samples of dispersion films, which comprises (a) providing an illuminated array of n spatially separated samples of the dispersion films, (b) imaging the array of n samples by means of a CCD camera at m+1 different times $t_0$ to $t_m$ and digitizing the images, (c) automatically determining a plurality of brightnesses $B(k, t_i)$ for each sample at different times $t_i$ selected from $t_0$ to $t_m$ from the m+1 different digitized images for at least a portion of the n samples, where $B(k, t_i)$ is the brightness of the kth of n samples at the respective time $t_i$ and is a measure for the blushing of this sample at this time, by averaging over the individual brightnesses of the individual pixels assigned to this sample, (d) determining values $P(k)$ of a parameter which is characteristic of the kinetics of the blushing from the different brightnesses $B(k, t_i)$ for each sample for at least a portion of the n samples, where $P(k)$ is the value of the characteristic parameter for the kth of the n samples.

For the purposes of the present invention, dispersion films are quite generally coating films based on polymer dispersions.

The process according to the invention employs a customarily rectangular array of n spatially separated samples of the dispersion films having areas of customarily from 1 $mm^2$ to 1 000 $cm^2$, preferably from 1 to 100 $cm^2$. A different geometry of the array, for example an approximately circular arrangement of the samples, is possible. The number n of the samples may, depending on the dimensions of the samples, be very large, for example, up to 10 000. The number n is at least two, customarily from 2 to 1 000 and preferably from 10 to 1 000. The samples are preferably rectangular and applied in a regular arrangement to a transparent or black substrate. For example, they may be prepared on a transparent foil such as a PET foil. The samples may also be arranged in a transparent sample holder having rectangular holes. The background below the transparent substrate is preferably black.

The array is preferably illuminated by a plurality of evenly distributed light sources, for example by two light sources arranged on opposite sides or by four light sources arranged on all four sides of a rectangular array. Even illumination is preferably achieved by using a highly diffuse light source, for example a white light lamp having a tungsten wire incandescent bulb.

Customarily, the process of blushing is initiated by wetting the samples with water. To this end, the samples are arranged in an appropriate container and the container is flooded with water. Blushing by wetting with aqueous solutions for certain substances or by liquids other than water may also be evaluated. Blushing of the samples under air may also be evaluated. Even the reverse process, ie the reduction of blushing after removal of water or the liquid, may also be evaluated.

Blushing of the dispersion films causes an increase in scattering of the incident light by the samples, which increases the brightness at the sample location.

The array of the n samples is imaged by means of a CCD camera at m+1 different times $t_0$ to $t_m$ and the images are digitized. m may be as large as desired, and is customarily from 10 to 1 000. The time resolution of the measurement, ie. the time interval between individual images depends on the likely rate of blushing and may, for example, be a second or even an hour. Digital imaging electronics, for example a frame grabber interface, are used to store the individual images in digital format in the memory of a control computer, for example a PC.

From the m+1 different digitized images, a plurality of brightnesses $B(k, t_i)$ at different times $t_i$ selected from $t_0$ to $t_m$ are automatically determined for each sample for at least a portion of the n samples. Preference is given to determining brightness values for each of the n samples at each of the m+1 times $t_0$ to $t_m$. This is sensible but not strictly necessary. Digitization of, for example, 8 bit assigns a brightness from 0 to 255 to each pixel. The brightness of a particular sample is determined by averaging the brightnesses of the pixels assigned to this sample. Since the number of pixels of every image of the CCD camera is very large, customarily from 500 000 to 1 000 000, there will be several hundred pixels for every individual sample in a number n of samples of, for example, 1 000. The averaging over many pixels still allows the measuring precision, even with a high number n of samples, to be high, ie distinctly higher than, for example, 8 bit.

Preference is given to carrying out the averaging after every imaging step and before the next imaging step, ie in real time. This considerably reduces the data quantity to be stored.

Preference is given to using the digitized images of the sample array to determine the brightnesses for a sample by averaging the brightnesses of pixels which have been assigned a certain predefined area of interest wholly within this sample. The size of the area of interest may, for example, correspond to a half or only a tenth of the sample area and may also vary from sample to sample. The location and size of the area of interest may be individually chosen before each measurement by the operator at the control computer for each sample or else be predefined according to a fixed pattern for all samples, while the latter requires a strictly regular arrangement of the samples in the array.

Preference is given to normalizing the brightnesses to a black surface which defines the zero value of blushing and to a white surface which defines the maximum value of blushing. To this end, the sample array is provided with a black and a white reference plate. Normalization compensates for variations in the illumination intensity during the measurement. A large number of samples may be analyzed by distributing a plurality of black and white reference plates in the array and normalizing each time using the nearest reference plates.

The resulting variations of brightness with time may be used to determine values P(k) of parameters for individual samples which characterize the kinetics of blushing. These values may be used to compare individual samples. For example, the variations of brightness with time may be defined by simple exponential functions, which give a rate constant for the kinetics of blushing as a characteristic parameter. Other sensible characteristic parameters include, for example, the time to 50% or 90% of a certain maximum brightness, or else the brightness which is attained after a predefined time.

The process according to the invention is a particularly simple process for determining the kinetics of blushing which facilitates a high sample throughput and, even at a high sample number, enables a sufficient measuring precision. It is therefore particularly suitable for coupling to combinatorial material research processes which comprise an automatic formulation of dispersions and an automatic coating of substrates. Such combinatorial material research processes typically involve a high throughput of samples to be characterized and therefore rely on a process for fast characterization of samples. Analysis of the large number of individual values obtained in this way for the characteristic parameter or parameters for the kinetics of blushing or the inverse process may reveal a systematic dependence on the composition of the dispersion formulations and the production conditions and show structure-effect relationships which allow the dispersions to be optimized with respect to their blushing behavior among other properties. For example, the type and the quantity ratio of the monomers contained in the dispersion polymers, the polymer architecture, the concentration of the different polymers and the auxiliaries in the dispersions and the conditions during the production of the coatings may be systematically varied.

The present invention accordingly also provides a device for parallel and automated evaluation of the blushing of dispersion films, which comprises:
(i) an array of n spatially separated samples of dispersion films;
(ii) one or more diffuse light sources for even illumination of the sample array;
(iii) a CCD camera disposed above the sample array for digital reproduction of the sample array;
(iv) digital imaging electronics;
(v) a control computer.

The invention is illustrated with reference to the drawings.

Figure 1:
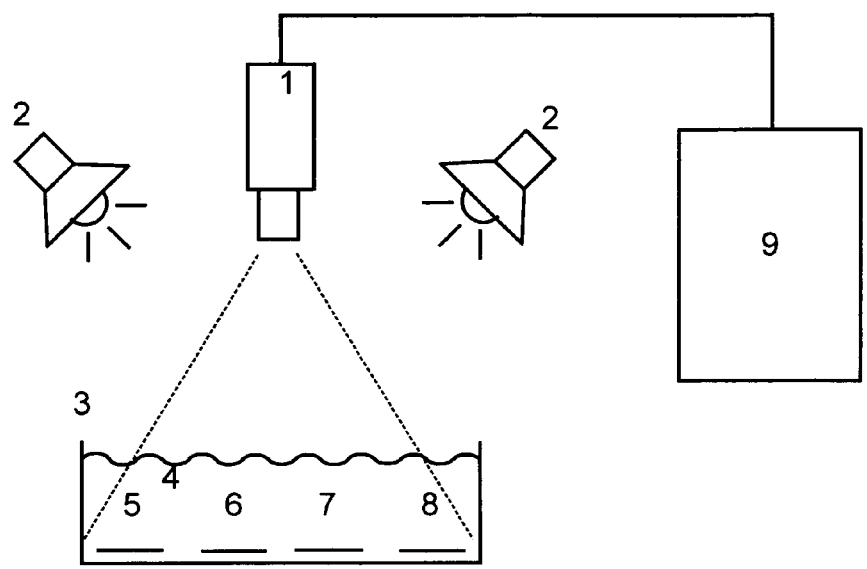
FIG. 1 shows a schematic of a suitable measuring arrangement in side view.
Figure 2:
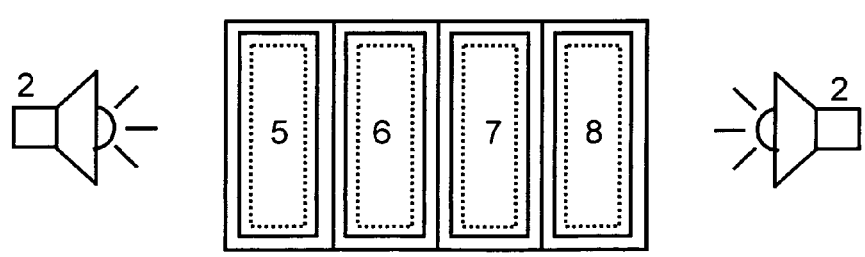
FIG. 2 shows a schematic of the same measuring arrangement in plan view.
Figure 3:
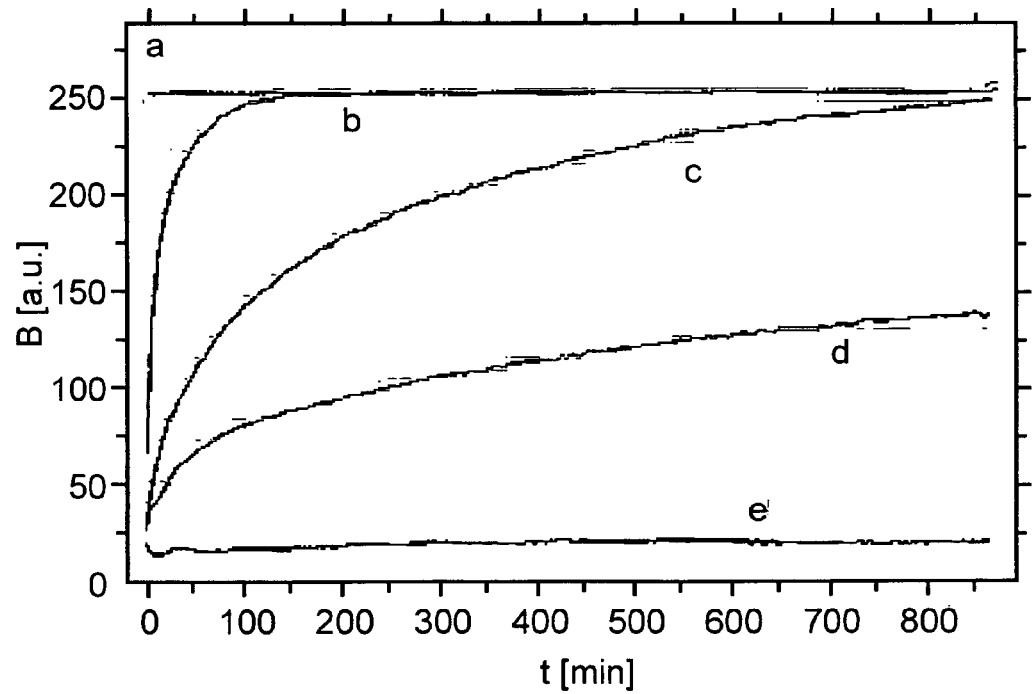
FIG. 3 shows examples of measured variations of brightness with time.

Samples of dispersion films 6 and 7 and reference plates 5 and 8 having areas of from 1 mm$^2$ to 1 000 cm$^2$ are arranged in an array and placed under a CCD camera 1 in a container 3. Samples of the dispersion films are applied to a transparent substrate such as a PET film or to a black substrate. When a transparent substrate is used, a black background is preferably chosen. In total, from 2-1 000 samples may be evaluated simultaneously. After the samples have been evenly flooded with water 4, the computer-controlled CCD camera 1 begins to take images at regular time intervals. Even lighting is preferably provided by two diffuse light sources on opposite sides. Increasing blushing results in stronger scattering of light incident on the samples and therefore an increase in brightness at the sample location. Digital imaging electronics, for example an image transformer card or a frame grabber interface, are used to store pictures in digital format in the memory of a control computer 9, for example a PC. A self-developed program continuously determines at variable intervals the average brightness of each of the evaluated samples over graphically variable areas of interest which are shown in FIG. 2 by dotted lines. Normalization to a black reference area 5 and a white reference area 8 allow normalization and the following of the variation of blushing with time, even at a varying illumination intensity. The kinetics of blushing of the individual samples may be continuously updated on the screen, for example by showing appropriate brightness/time curves. Examples of such curves are shown in FIG. 3. The repeat frequency and overall duration of the measurement are variable. The inverse process, ie the reduction of blushing after removal of water, may also be followed. The brightness/time variations may be described by simple exponential curves. This facilitates the comparability of different samples with the use of rate constants, characteristic times and/or maximum achievable brightnesses.

We claim:
1. A process for parallel and automated evaluation of the blushing of n samples of dispersion films, which comprises:
(a) providing an illuminated array of n spatially separated samples of the dispersion films,
(b) imaging the array of n samples by means of a CCD camera at m+1 different times $T_0$ to $t_m$ and digitizing the images,
(c) automatically determining a plurality of brightnesses $B(k, t_i)$ for each sample at different times $T_i$ selected from $t_0$ to $t_m$ from the m+1 different digitized images for at least a portion of the n samples, where $B(k, t_i)$ is the brightness of the kth of n samples at the respective time $t_i$ and is a measure for the blushing of this sample at this time,
(d) determining a value P(k) of a parameter which is characteristic of the kinetics of the blushing from the different brightnesses $B(k, t_i)$ for each sample for at least a portion of the n samples, where P(k) is the value of the characteristic parameter for the kth of the n samples,
(e) comparing the value P(k) for individual samples.

2. A process as claimed in claim 1, wherein the brightnesses are normalized to a black surface as a zero value of blushing and to a white surface as a maximum value of blushing.

3. A process as claimed in claim 1, wherein the brightnesses of a sample are determined from a digitized image of a sample array by averaging the brightnesses of all pixels which are assigned to a certain area of interest within this sample.

4. A process as claimed in claim 1, wherein the number n of the samples is from 2 to 1 000.

* * * * *